United States Patent [19]

Kordes

[11] Patent Number: Plant 7,509

[45] Date of Patent: Apr. 30, 1991

[54] ROSE PLANT KORBOLAK

[75] Inventor: Wilhelm Kordes, Sparrieshoop, Fed. Rep. of Germany

[73] Assignee: Bear Creek Gardens, Inc., Medford, Oreg.

[21] Appl. No.: 475,955

[22] Filed: Feb. 6, 1990

[51] Int. Cl.[5] ..... A01H 5/00

[52] U.S. Cl. ..... Plt./18

[58] Field of Search ..... Plt./18

*Primary Examiner*—James R. Feyrer

*Attorney, Agent, or Firm*—Klarquist, Sparkman, Campbell, Leigh & Whinston

[57] ABSTRACT

A hybrid tea rose variety having high yield (200–220 stems/m$^2$), exceptionally long vase life (ten days or more), long stems (average 70–80 cm), disease resistant foliage, and very long bud and large flower size.

1 Drawing Sheet

This present invention relates to a new and distinct variety of rose plant named Korbolak of the hybrid tea class which was originated by me by crossing the variety Lorena, U.S. Plant Pat. No. 5,679, with the variety Emily Post.

The primary objective of this breeding was to produce a new rose variety having high cut flower yield, long stems, good vase and an attractive high centered flower. The objective was substantially achieved along with other desirable improvements as evidenced by the following unique combination of characteristics which are outstanding in the new variety and which distinguish it from its parents as well as from all other varieties of which I am aware:

1. High yield (200–220 stems/m$^2$).
2. Exceptionally long vase life (ten (10) days or more).
3. Long stems (average 70–80 cm).
4. Disease resistant foliage.
5. Very long bud and large flower size.

Asexual reproduction of this new variety by budding, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color in terminology in accordance with the Royal Horticultural Society Colour Chart except where ordinary dictionary significance of color is indicated.

Parentage:

*Seed parent.*—Lorena, U.S. Plant Pat. No. 5,679.

*Pollen parent.*—Emily Post.

Classification:

*Botanical.*—*Rosa hydrida.*

*Commercial.*—Hybrid tea.

FLOWER

Observations made from specimens grown in a greenhouse environment in Somis, Calif.

Blooming habit: Recurrent.

Bud:

*Size.*—2 to 2½ inches when the petals start to unfurl.

*Form.*—Long to very long, pointed ovoid.

*Color.*—When sepals first divide: Red Group 49B. When half blown: The upper sides of the petals are Red Group 49B to C; and the lower sides of the petals are Red Group 49B.

*Sepals.*—Color: Greyed green 195B. Surface texture: Covered in fine hairs. Three normally appendaged sepals and two unappendaged sepals with hairy edges.

*Receptacle.*—Color: Medium green. Shape: Funnel. Size: Medium. Surface: Smooth.

*Peduncle.*—Length: Medium. Surface: Smooth with occasional small prickle. Color: Medium green. Strength: Stiff, erect.

Bloom:

*Size.*—Large. Average open size is 4½ inches.

*Borne.*—Singly.

*Stems.*—Long, strong.

*Form.*—When first open: High centered. Permanence: Retains its form to the end, outer petal edges curl slightly.

*Petalage.*—Number of petals under normal conditions: 30 to 35.

*Color.*—Upper side of petals is: Red Group 49B to C. Reverse side of petals is: Red Group 49C. Base of petals is: Distinct yellow half moon. Major color on the upper side is: Red Group 49C.

*Variegations.*—Occasional green streak on the outer guard petals.

*Discoloration.*—General tonality at end of first day: No change; at the end of the third day: No change.

*Fragrance.*—Slight.

Petals:

*Texture.*—Thick.

*Shape.*—Round.

*Form.*—Tips slightly recurved.

*Arrangement.*—Imbricated.

*Persistence.*—Drop off cleanly.

*Lastingness.*—On the plant: Very long. As a cut flower: Very long.

Reproductive parts:

*Anthers.*—Size: Large. Quantity: Many. Color: Yellow. Arrangement: Regular around styles.

*Filaments.*—Color: White.

*Pollen.*—Color: Lemon yellow.

*Styles.*—Color: Pink.

*Stigmas.*—Color: Greenish white.

Form: Bush.

Growth: Very vigorous, upright.

Foliage:

*Number of leaflets on normal mid-stem leaves.*—5.

*Size.*—Large.

*Quantity.*—Normal.

*Color.*—New foliage: Reddish. Old foliage: Dark green.

Leaflets:

*Shape.*—Oval.

*Texture.*—Leathery.

*Edge.*—Serrated.

*Serration.*—Single, small.

*Petiole.*—Rachis: Reddish. Underside: Smooth with prickles.

*Stipules.*—Medium, bearded.

*Disease resistance.*—Resistant to powdery mildew under normal growing conditions at Somis, Calif.

Wood:

*New wood.*—Color: Reddish. Bark: Smooth.

*Old wood.*—Color: Green. Bark: Smooth.

Prickles:

*Quantity.*—On main canes from base: Many. On laterals from main canes: Many.

*Form.*—Medium, hooked downward.

*Color when young.*—Red.

Small prickles:

*Quantity.*—On main stalks: Few. On laterals: Few.

*Color.*—Green.

I claim:

1. A new and distinct variety of rose plant of the hybrid tea class, substantially as herein shown and described, characterized particularly as to novelty by its exceptionally high yield of long stemmed roses, its large flower size, its very long vase life, and its healthy disease resistant foliage.

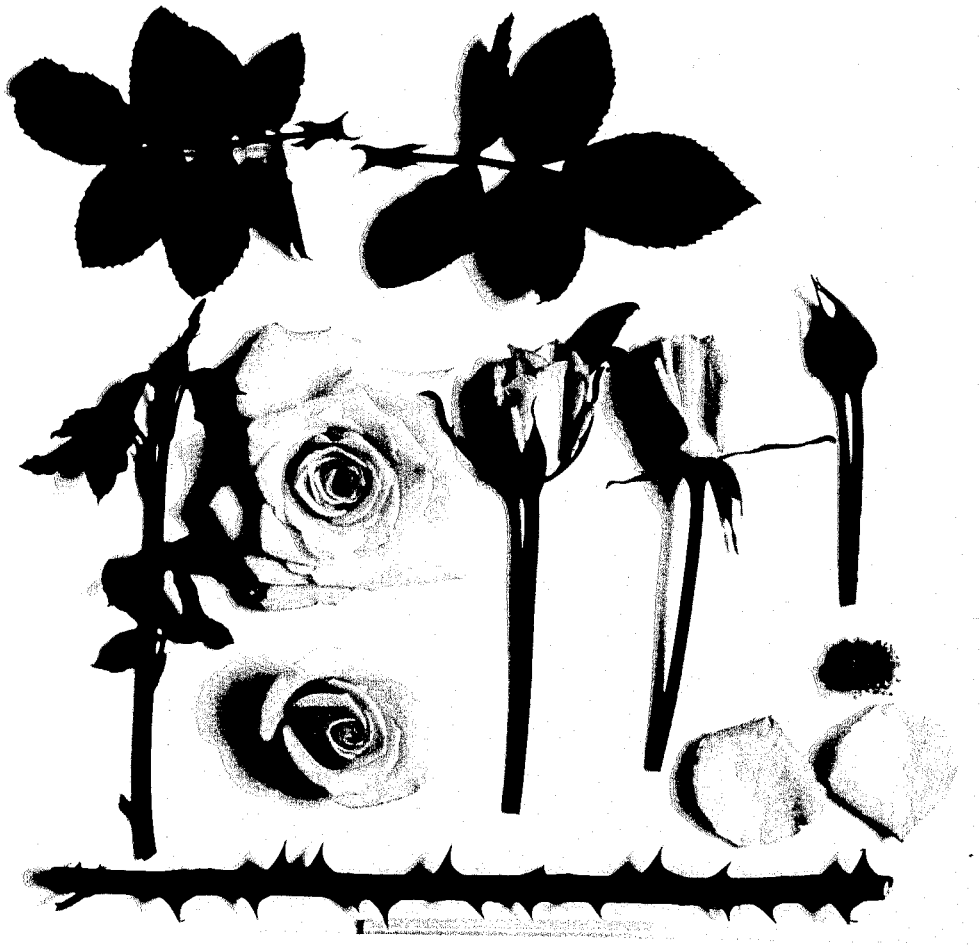

* * * * *